United States Patent [19]

Audousset

[11] Patent Number: 5,711,765

[45] Date of Patent: Jan. 27, 1998

[54] PROCESS FOR THE DIRECT DYEING OF HUMAN KERATIN FIBRES USING CATIONIC DYES AND WATER VAPOR

[75] Inventor: Marie-Pascale Audousset, Asnieres, France

[73] Assignee: L'Oreal, Paris, France

[21] Appl. No.: 723,834

[22] Filed: Sep. 30, 1996

Related U.S. Application Data

[63] Continuation of Ser. No. 531,007, Sep. 20, 1995, abandoned.

[30] Foreign Application Priority Data

Sep. 21, 1994 [FR] France .................................. 94 11265

[51] Int. Cl.$^6$ .......................................................... A61K 7/13
[52] U.S. Cl. .............................. 8/426; 8/657; 8/933
[58] Field of Search .......................... 8/404, 405, 426, 8/654, 657, 917, 933

[56] References Cited

U.S. PATENT DOCUMENTS

| 4,166,473 | 9/1979 | Bauer et al. ......................... | 132/9 |
| 4,341,229 | 7/1982 | Bauer et al. ......................... | 132/7 |
| 5,104,413 | 4/1992 | Ikeda ................................. | 8/405 |

FOREIGN PATENT DOCUMENTS

| A-0103547 | 3/1984 | European Pat. Off. . |
| A-1011151 | 6/1952 | France . |
| A-1157665 | 6/1958 | France . |
| A-2273492 | 1/1976 | France . |
| A-4235436 | 4/1993 | Germany . |
| u-9318614 | 1/1994 | Germany . |
| A-357161 | 11/1961 | Switzerland . |
| A-2168082 | 6/1986 | United Kingdom . |

OTHER PUBLICATIONS

English language translation of FR 1,011,151, AMICA Co., pp. 1–14, Jun. 1952.

Colour Index, Third Edition, vol. 4, The Society of Dyes and Colourists, p. 4470, C1 #52020, 1971.

*Primary Examiner*—Paul Lieberman
*Assistant Examiner*—Caroline L. Dusheck
*Attorney, Agent, or Firm*—Finnegan, Henderson, Farabow, Garrett & Dunner

[57] ABSTRACT

A process for the direct dyeing of keratin fibers, characterized in that it comprises in placing keratin fibers, to which a dye composition containing at least one cationic direct dye has been applied, in contact with a gas containing water vapor, the temperature of the gas preferably being above 75° C., the contact time between the gas and the fibers to be dyed preferably not exceeding two minutes. According to the invention, the hair is dyed uniformly, from the roots to the tips, regardless of the state of the hair.

22 Claims, No Drawings

PROCESS FOR THE DIRECT DYEING OF HUMAN KERATIN FIBRES USING CATIONIC DYES AND WATER VAPOR

This application is a continuation of application Ser. No. 08/531,007, filed Sep. 20, 1995, now abandoned.

The present invention is directed to a process for the direct dyeing (or tinting) of keratin fibres using water vapour and a dye composition comprising at least one cationic direct dye.

The use of cationic dyes for the direct dyeing of keratin fibres, and in particular human keratin fibres such as the hair, is well known in the state of the art. On account of their cationic nature, these direct dyes have a good affinity for the fibres. These cationic dyes form a fairly varied range of colours, allowing all tones to be formulated.

However, these dyes are very sensitive to the degree of sensitization (i.e. the state of degradation) of keratinous fibre. That is, these dyes are selective.

The selectivity of a dye refers to the difference in rise, i.e., of dyeing power, of the dye on the hair fibres or the various parts thereof depending on whether the fibres have been more or less sensitized or "damaged", either by a treatment, such as bleaching or permanent-waving, or by atmospheric agents.

The dyeing results obtained on hair having differences in sensitization are thus heterogeneous. These irregularities are obviously not desirable from an aesthetic point of view.

The present invention aims to overcome the above problem.

The Inventor has now discovered, surprisingly, that the use of a gas comprising water vapour, preferably heated to a temperature greater than 75° C., on hair treated with at least one cationic direct dye, made it possible to obtain dyeing results which were quite independent of the degree of sensitization of the keratin fibres which were dyed.

According to the invention, the hair is thus dyed uniformly from the roots to the tips over the whole head of hair or over certain selected locks, regardless of the state of the hair.

The dyeing is very rapid and the hair displays excellent cosmetic properties.

It is noted that the use of water vapour in an oxidation dyeing process has already been described in French Patent No. 1,011,151, the disclosure of which is incorporated herein by reference. This French patent discloses that the use of water vapour heated to approximately 50° C. can be used to accelerate the process of oxidation dyeing of the hair, while at the same time reducing the amounts of dyes used. However, at approximately 50° C., there is no decrease in the selectivity, as there is for the cationic dyes discussed above.

The present invention is thus directed to a process for the direct dyeing of keratin fibres to lower selectivity thereon, which comprises directly dyeing the fibres to lower the selectivity by applying to the keratin fibres a dye composition containing at least one cationic direct dye and contacting the keratin fibres with a gas containing water vapour; the gas having a temperature greater than 75° C. for a contact time between the gas and the keratin fibres not exceeding two minutes.

The present invention is also directed to a process for the direct dyeing of keratin fibres to lower selectivity thereon, which comprises directly dyeing the fibres to lower the selectivity by applying to the fibres a dye composition containing at least one cationic direct dye; and contacting the fibres with a gas containing water vapour, the gas having a temperature greater than 75° C., for a contact time between the gas and the fibres being sufficient at the temperature to lower the selectivity.

The present invention also contemplates a process for the direct dyeing of keratin fibres to lower selectivity thereon, which comprises directly dyeing the fibres to lower the selectivity by applying to the fibres a dye composition containing at least one cationic direct dye; and contacting the fibres with a gas containing water vapour, the temperature of the gas and the contact time between the gas and the fibres being sufficient to lower the selectivity.

A further embodiment of the present invention includes a process for the direct dyeing of keratin fibres to lower selectivity thereon, which comprises directly dyeing the fibres to lower the selectivity by applying to the fibres a dye composition containing at least one cationic direct dye; and contacting the fibres with a gas containing water vapour, for a time not exceeding two minutes, and wherein the gas has a sufficient temperature for the time to lower the selectivity.

The cationic direct dyes which may be used according to the invention may be chosen, for example, from cationic triarylmethane dyes, cationic naphthoquinones, cationic anthraquinones, cationic methines, cationic thiazines, cationic azo dyes, cationic oxazines, cationic nitro dyes, and salts of these compounds.

Cationic triarylmethane dyes which may be mentioned, for example, are bis-4,4'-dimethylaminophenyl-4"-phenylaminonaphthylcarbenium chloride, referred to as Basic Blue 7 (CI 42595) in the third edition of the Color Index, bis-(4,4'-diethylamino)triphenylcarbenium hydrosulphate, referred to as Basic Green 1 (CI 42040), 4,4,4"-triamino-2-methyltriphenylcarbenium chloride tetrahydrate, referred to as Basic Violet 14 (CI 42510), 2,8-dimethyl-3,7-diamino-5-phenylphenazinium chloride, referred to as Basic Red 2 (CI 50240), Basic Blue 26 (CI 44045) and Basic Violet 3 (CI 42555).

A cationic naphthoquinone dye which may be mentioned, for example, is 2-bromo-4,8-diamino-6-(3'-trimethyl-ammonium)phenylamino-1,5-naphthoquinone chloride, referred to as Basic Blue 99 (CI 56059).

Among the cationic anthraquinones which may be mentioned, by way of example, are 1-methylamino-4-(γ-aminopropyl)-aminoanthraquinone hydrochloride, 1-(N-methylmorpholiniumpropylamino)-4-hydroxy-anthraquinone methyl sulphate and Basic Blue 22 (CI 61512).

Among the cationic methines which may be mentioned, by way of example, is Basic Yellow 29.

Among the cationic thiazines which may be mentioned, by way of example, is Basic Blue 9.

Among the cationic azo dyes which may be mentioned, by way of example, are 1-(2'-methoxyphenylazo)-2-hydroxy-7-trimethylammoniumnaphthalene chloride referred to as Basic Red 76 (CI 12245), 4-(3'-trimethylammonium-phenylazo)-N-phenyl-3-methyl-5-pyrazolone chloride, referred to as Basic Yellow 57 (CI 12719), 1-(4'-amino-phenylazo)-2-hydroxy-7-trimethylammoniumnaphthalene chloride, referred to as Basic Brown 16 (CI 12250) and 1-(2'-nitro-4'-aminophenylazo)-2-hydroxy-7-trimethylammoniumnaphthalene, referred to as Basic Brown 17 (CI 12251).

Among the cationic oxazines which may be mentioned, by way of example, is Basic Blue 3 (CI 51004).

The cationic nitro dyes are preferably chosen from the cationic nitro derivatives of the benzene series. Such compounds are described, for example, in French Patents FR 1

506 350, FR 1 508 405, and FR 1 565 261, and in U.S. Pat. No. 5,298,029, the disclosure of each of which is incorporated herein by reference.

Among these compounds, there may more particularly be mentioned β-[N-methyl-N-(3-nitro-4-N'-methylamino) phenyl]-aminoethylmethylpiperidinium iodide, β-[N-(2-nitro-4-N'-methylamino)phenyl] aminoethylmethylpiperidinium iodide, β-[N-(2-nitro-4-amino)phenyl]aminoethylmethylpiperidinium iodide, γ-[N-(2-nitro-4-methyl-5-amino)phenyl]aminopropyl-trimethylammoniummethyl sulphate, γ-[N-(2-nitro-5-dimethylamino)phenyl]aminopropyltrimethylammonium methyl sulphate, β-[N-(3-dimethylamino-4-nitro-6-methyl) phenyl]-aminoethylmethyldiethylammonium methyl sulphate, β-[N-(2-nitro-N'-methyl-N'-benzenesulphonyl-4-amino)phenyl]-aminoethylmethyldiethylammonium methyl sulphate, dimethylhexadecyl-2-(2-nitroanilino) ethylammonium iodide, diethyl-2-(2-nitroanilino) ethyltetradecylammonium iodide and dimethylhexadecyl-2-(5-methyl-2-nitroanilino)ethyl-ammonium bromide.

The cationic direct dyes used according to the process of the invention are preferably present in concentrations ranging from 0.01 to 10% by weight, and even more preferably from 0.05 to 5% by weight, relative to the total weight of the dye composition.

In addition to water vapour, the carrier gas may contain solvent vapour, gases such as oxygen and nitrogen, gas mixtures, such as air, or vaporizable compounds.

The solvents which may be used for the production of vapour may be chosen from cosmetically acceptable organic solvents, and more particularly from alcohols, such as ethanol, isopropanol, benzyl alcohol, and phenylethyl alcohol, or glycols or glycol ethers, such as, for example, ethylene glycol monomethyl, monoethyl and monobutyl ethers, propylene glycol, butylene glycol, dipropylene glycol and the alkyl ethers such as diethylene glycol monobutylether.

The gas preferably comprises at least 1% by volume of water vapour relative to the total volume of the gas.

The gas preferably consists either exclusively or essentially of water vapour, or of a mixture of water vapour and air.

The temperature of the gas is preferably at least 85° C., more preferably ranges from 85° to 150° C., still more preferably ranges from 85° to 100° C., and even more preferably ranges from 90° to 100° C.

Preferably, the gas is contacted with the fibres to be dyed for a time period ranging from 0.01 second to 2 minutes. More preferably, the gas is contacted with the fibres for a time period ranging from 0.1 second to 50 seconds, and even more preferably for a time period ranging from 1 to 10 seconds.

Contacting of the gas and fibres may be repeated several times on the fibres, each application taking place according to the time periods mentioned above.

In a first embodiment of the process according to the invention, which is preferred, a dye composition containing at least one cationic direct dye is applied to the hair, which hair is then subjected to the action of the gas containing water vapour.

According to another preferred embodiment of the process, it is possible to simultaneously apply the dye composition and the gas comprising water vapour.

It is also possible to put all or some of the dye composition on the hair by means of the gas flow when some or all of the constituents of the formula can be entrained or vaporized.

The application of water vapour is optionally followed by an operation of rinsing with water.

A hot gas comprising water vapour may be produced using any apparatus which is known per se. However, according to the present invention, an apparatus such as that described in French Patent Application FR-A-2,273,492, the disclosure of which is incorporated herein by reference, or any other equivalent apparatus which is particularly suitable, is preferably used.

The dye compositions used in accordance with the invention may be in forms conventionally used for dyeing hair, such as a liquid which is more or less thickened or gelled, a cream, an aerosol foam, or any other form which is suitable for dyeing the hair.

The dye compositions used in accordance with the invention are generally aqueous compositions which may contain ingredients usually used in cosmetic compositions intended to dye the hair, such as solvents, surface-active agents, thickeners, treating agents, basifying or acidifying agents, preserving agents, fragrances or any other additive used in this type of composition.

The dye composition containing at least one cationic direct dye has a pH which preferably ranges from 2 to 11, and which more preferably ranges from 5 to 9.

The dye composition may also be in the form of an anhydrous solution or powder which is diluted at the time of use with water or an aqueous support. The powders thus employed give a poultice. The anhydrous solutions may be applied directly to the wet hair. The supports are described, for example, in French Patent Applications FR-A-2,500,749, FR-A-2,598,318, FR-A-2,526,031 and FR-A-2,500,748, the disclosures of which are incorporated herein by reference.

The examples which follow illustrate the invention without, however, being limiting in nature.

EXAMPLE 1

Invention

The following dye composition was prepared:

| | |
|---|---|
| Mixture of cetylstearyl alcohol and cetylstearyl alcohol oxyethylenated with 33 mol of ethylene oxide (80/20) | 2 g |
| Nonylphenol oxyethylenated with 40 mol of ethylene oxide | 3 g |
| Nonylphenol oxyethylenated with 90 mol of ethylene oxide | 2 g |
| $C_{16}/C_{18}/C_{18}$ (25/25/50) oleocetyldimethylhydroxyethylammonium chloride as a 30% aqueous solution | 16.6 g |
| 2-Butoxyethanol | 8 g |
| Basic Blue 3, referred to as CI 51004 in the 3rd edition of the CTFA | 0.1 g |
| Monoethanolamine qs | pH 7 |
| Demineralized water qs | 100 g |

This dye composition was applied to a lock of natural hair, that is to say non-sensitized hair (lock No. 1) and to a lock of this same hair which had undergone a permanent-waving (lock No. 2).

A jet of water vapour at 90° C. was then applied to the two locks for 45 seconds. The locks were next rinsed and then dried.

The shades obtained were similar. The colour of the locks was then evaluated in the Munsell system using a Minolta CM 2002 colorimeter.

According to the Munsell notation, a colour is defined by the expression HV/C in which the three parameters respectively denote the tint (H), the intensity (V) and the purity (C). The oblique line in this expression is simply a convention and does not indicate a ratio. The difference in colour between two locks is calculated by applying the Nickerson formula: ΔE=0.4 CodH+6 dV+3 dC, as described, for example, in "Couleur, Industrie et Technique", pages 14–17; Vol No. 5; 1978.

In this formula, ΔE represents the difference in colour between two locks, dH, dV and dC represent the variation in absolute value of the parameters H, V and C, and Co represents the purity of the lock with respect to which it is desired to evaluate the difference in colour.

The results are expressed in the table below:

| Colour on natural hair | Colour on permanent-waved hair | Colour difference | | | |
|---|---|---|---|---|---|
| | | dH | dV | dC | ΔE |
| 9.8 G 4.6/2.4 | 3.9 BG 4.6/3.2 | 4.1 | 0 | 0.8 | 6.3 |

The difference in colour between the lock of natural hair (lock No. 1) and the lock of permanent-waved hair (lock No. 2) was small, which is indicative of a uniform colouration.

EXAMPLE 2

Comparative

The dye composition of Example 1 was applied to a lock of non-sensitized natural hair, identical to that used in Example 1 above (lock No. 1), and to a lock of the same hair which had undergone a permanent-waving operation (lock No. 2).

Instead of using the process of the invention, the composition was left to stand on the locks for 30 minutes at room temperature. The locks were then rinsed and dried.

The difference in colour between the two locks was evaluated as in Example 1. The results are expressed in the table below:

| Colour on natural hair | Colour on permanent-waved hair | Colour difference | | | |
|---|---|---|---|---|---|
| | | dH | dV | dC | ΔE |
| 1.9 BG 4.5/2.8 | 6.6 BG 4.6/4.8 | 4.7 | 0.1 | 2.0 | 11.9 |

A large difference in colour was observed between the locks of natural hair and the locks of permanent-waved hair, which is indicative of a non-uniform and thus a selective colouration according to the state of degradation of the hair.

EXAMPLE 3

Invention

The following dye composition was prepared:

| | |
|---|---|
| Mixture of cetylstearyl alcohol and cetylstearyl alcohol oxyethylenated with 33 mol of ethylene oxide (80/20) | 2 g |
| Nonylphenol oxyethylenated with 40 mol of ethylene oxide | 3 g |
| Nonylphenol oxyethylenated with 90 mol of ethylene oxide | 2 g |
| $C_{16}/C_{18}/C_{18}$ (25/25/50) oleocetyldimethylhydroxyethylammonium chloride as a 30% aqueous solution | 16.6 g |
| 2-Butoxyethanol | 8 g |
| Basic Blue 99, referred to as CI 56059 in the 3rd edition of the CTFA | 0.15 g |
| Monoethanolamine qs | pH 7 |
| Demineralized water qs | 100 g |

This dye composition was applied to a lock of natural hair, that is to say non-sensitized hair (lock No. 1) and to a lock of this same hair which had undergone a permanent-waving (lock No. 2).

A jet of water vapour at 90° C. was then applied to the two locks for 45 seconds, and the locks were next rinsed and then dried.

The difference in colour between the two locks was then evaluated as in Example 1.

The results are expressed in the table below:

| Colour on natural hair | Colour on permanent-waved hair | Colour difference | | | |
|---|---|---|---|---|---|
| | | dH | dV | dC | ΔE |
| 2.2 BG 4.2/1.1 | 6.9 BG 4.3/1.3 | 4.7 | 0.1 | 0.2 | 3.3 |

The difference in colour between the lock of natural hair (lock No. 1) and the lock of permanent-waved hair (lock No. 2) was small, which is indicative of a uniform colouration.

EXAMPLE 4

Comparative

The dye composition of Example 3 was applied to a lock of non-sensitized natural hair, identical to that used in Example 3 above (lock No. 1), and to a lock of the same hair which had undergone a permanent-waving operation (lock No. 2).

Instead of using the process of the invention, the composition was left to stand on the locks for 30 minutes at room temperature. The locks were then rinsed and dried.

The difference in colour between the two locks was evaluated as in Example 1. The results are expressed in the table below:

| Colour on natural hair | Colour on permanent-waved hair | Colour difference | | | |
|---|---|---|---|---|---|
| | | dH | dV | dC | ΔE |
| 8.6 BG 4.1/1.3 | 4.5 B 3.7/1.9 | 5.9 | 0.4 | 0.6 | 7.3 |

It was observed that the difference in colour between the two locks was larger than that obtained in Example 3 above. The dyeing obtained according to this process, which did not form part of the invention, was thus less uniform than that obtained above in Example 3.

What is claimed is:

1. A process for the direct dyeing of keratin fibres which have differences in sensitization to lower selectivity thereon, which comprises directly dyeing said fibres to lower said selectivity by applying to said keratin fibres a dye composition containing at least one cationic direct dye selected from cationic naphthoquinone and anthraquinone dyes, cationic methine dyes, cationic azo dyes, cationic oxazine dyes, and the salts of said compounds; and contacting said keratin fibres with a gas containing water vapour, said gas having a temperature greater than 75° C., for a contact time between said gas and said keratin fibres not exceeding two minutes.

2. The process according to claim 1, wherein the gas has a temperature of at least 85° C.

3. The process according to claim 2, wherein the gas has a temperature ranging from 85 to 150° C.

4. The process according to claim 1, wherein the gas is contacted with the keratin fibres to. be dyed for a period of time ranging from 0.01 second to not exceeding 2 minutes.

5. The process according to claim 4, wherein the gas is contacted with the keratin fibres for a period of time ranging from 0.1 second to 50 seconds.

6. The process according to claim 5, wherein the gas is contacted with the keratin fibres to be dyed for a period of time ranging from i second to 10 seconds.

7. The process according to claim 1, wherein the contacting of said fibres with said gas is repeated several times on the fibres.

8. The process according to claim 1, wherein the gas contains exclusively water vapour.

9. The process according to claim 1, wherein the gas contains water vapour and at least one other compound in the form of gas or vapour.

10. The process according to claim 9, wherein the gas contains water vapour and air.

11. The process according to claim 1, wherein said at least one cationic direct dye is present in a concentration ranging from 0.01 to 10% by weight relative to the total weight of said composition.

12. The process according to claim 11, wherein said at least one cationic direct dye is present in a concentration ranging from 0.05 to 5% by weight relative to the total weight of the dye composition.

13. The process according to claim 1, wherein said keratinous fibres are human keratinous fibres.

14. The process according to claim 1, wherein said fibres are contacted with said gas containing water vapour simultaneously with said fibres being contacted with said dye composition containing at least one cationic direct dye.

15. The process according to claim 1, wherein said fibres are contacted with said gas containing water vapour subsequent to said fibres being contacted with said dye composition containing at least one cationic direct dye.

16. The process according to claim 1, wherein said gas has a temperature ranging from greater than 75° C. to less than 100° C.

17. The process according to claim 16, wherein said gas has a temperature ranging from 85° C. to less than 100° C.

18. The process according to claim 17, wherein said gas has a temperature ranging from 90° C. to less than 100° C.

19. The process according to claim 1, wherein the pH of said dye composition containing at least one cationic dye ranges from 2 to 11.

20. The process according to claim 19, wherein the pH of said dye composition ranges from 5 to 9.

21. A process according to claim 1, wherein said at least one cationic direct dye is selected from cationic naphthoquinone dyes, cationic methine dyes, cationic azo dyes, cationic oxazine dyes, and the salts of said compounds.

22. A process according to claim 1, wherein said at least one cationic direct dye is selected from cationic methine dyes, cationic azo dyes and the salts of said compounds.

* * * * *

UNITED STATES PATENT AND TRADEMARK OFFICE
CERTIFICATE OF CORRECTION

PATENT NO. : 5,711,765
DATED : January 27, 1998
INVENTOR(S) : Marie-Pascale AUDOUSSET It is certified that error appears in the above-identified patent and that said Letters Patent is hereby corrected as shown below:

On the title page, item [54] and col. 1, line 1
In the Title, "vapor" should read --vapour--.

In the Claims, claim 4, column 7, line 14, delete " to. be dyed ";

claim 6, column 7, line 20, delete "to be dyed";

line 21, "i second" should read --1 second--.

Signed and Sealed this

Twenty-first Day of April, 1998

Attest:

BRUCE LEHMAN

Attesting Officer

Commissioner of Patents and Trademarks